US012636416B2

(12) United States Patent
Fällman et al.

(10) Patent No.: US 12,636,416 B2
(45) Date of Patent: May 26, 2026

(54) PERITONEAL DIALYSIS SYSTEM HAVING DISINFECTION GAS RELIEF

(71) Applicants: BAXTER INTERNATIONAL INC., Deerfield, IL (US); BAXTER HEALTHCARE SA, Glattpark (CH)

(72) Inventors: Oskar Erik Frode Styrbjörn Fällman, Lund (SE); Per-Olof Borgqvist, Lund (SE); Bjorn Ericson, Lund (SE); Markus Nilsson, Lund (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 402 days.

(21) Appl. No.: 18/335,367

(22) Filed: Jun. 15, 2023

(65) Prior Publication Data

US 2023/0414852 A1     Dec. 28, 2023

Related U.S. Application Data

(60) Provisional application No. 63/354,523, filed on Jun. 22, 2022.

(51) Int. Cl.
| | |
|---|---|
| *A61M 39/24* | (2006.01) |
| *A61M 1/16* | (2006.01) |
| *A61M 1/28* | (2006.01) |

(52) U.S. Cl.
CPC .......... *A61M 1/282* (2014.02); *A61M 1/1686* (2013.01); *A61M 1/1688* (2014.02); *A61M 1/169* (2013.01); *A61M 1/281* (2014.02); *A61M 1/288* (2014.02); *A61M 39/24* (2013.01); *A61M 2205/0205* (2013.01); *A61M 2205/3331* (2013.01)

(58) Field of Classification Search
CPC .. A61M 1/1686; A61M 1/1688; A61M 1/169; A61M 1/281; A61M 1/282; A61M 1/288; A61M 39/24; A61M 2205/0205; A61M 2205/3331
See application file for complete search history.

(56) References Cited

U.S. PATENT DOCUMENTS

2016/0243540 A1 * 8/2016 Menon ..................... B01J 39/12

FOREIGN PATENT DOCUMENTS

EP           3466460 A1 * 4/2019
WO       WO 00/57935 A1 * 10/2000

* cited by examiner

*Primary Examiner* — John Kim
(74) *Attorney, Agent, or Firm* — K&L Gates LLP

(57) ABSTRACT

A peritoneal dialysis ("PD") system includes a PD fluid pump, a disinfection loop including the PD fluid pump, the disinfection loop including PD fluid used for disinfecting the disinfection loop, and an acid solution source positioned and arranged to supply an acid solution to the disinfection loop during disinfection using the PD fluid. The disinfection loop includes an airtrap and a pressure sensor positioned and arranged to sense PD fluid pressure during disinfection, the pressure sensor outputting to a control unit, the control unit configured to open at least one gas valve located along at least one gas line leading to an upper portion of the airtrap when the PD fluid pressure reaches or exceeds a threshold PD fluid pressure due to gas formation caused by mixing the acid solution with the PD fluid.

20 Claims, 7 Drawing Sheets

PERITONEAL DIALYSIS SYSTEM HAVING DISINFECTION GAS RELIEF

PRIORITY CLAIM AND CROSS-REFERENCE TO RELATED APPLICATION

This application claims priority to and the benefit of U.S. Provisional Patent Application No. 63/354,523, filed Jun. 22, 2022, titled PERITONEAL DIALYSIS SYSTEM HAVING DISINFECTION GAS RELIEF, the entire contents of which are incorporated by reference herein in their entirety and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. PD machines, however, perform the cycles automatically, typically while the patient sleeps. PD machines free patients from having to manually perform the treatment cycles and from having to transport supplies during the day. PD machines connect fluidly to an implanted catheter, to a source or bag of fresh dialysis fluid and to a fluid drain. PD machines pump fresh dialysis fluid from a dialysis fluid source, through the catheter and into the patient's peritoneal chamber. PD machines also allow for the dialysis fluid to dwell within the chamber and for the transfer of waste, toxins and excess water to take place. The source may include multiple liters of dialysis fluid including several solution bags.

PD machines pump used or spent dialysate from the patient's peritoneal cavity, though the catheter, to drain. As with the manual process, several drain, fill and dwell cycles occur during dialysis. A "last fill" may occur at the end of the PD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an PD machine that reduces disposable waste. In doing so, to the extent that deposits of calcium carbonate are created via disinfection, such deposits may be prevented via the introduction of an acid solution. A product gas resulting from the introduction of the acid solution may be released into the disinfected tubing of the PD machine. A need exists accordingly for a way to release such gas.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

The PD system and associated methodology of the present disclosure, on the other hand, convert much of the fluid carrying portions of its PD system into reusable components, which are disinfected after treatment. Fluid lines within the machine or cycler are reused. Disposable items remaining may include a drain line leading to a drain bag or house drain and one or more PD fluid container or bag, such as different dextrose or glucose level PD fluid containers and a last bag container, e.g., containing icodextrine. In an embodiment, a disposable filter is placed at the distal end of the patient line to provide a final stage of PD fluid filtration prior to delivery to the patient.

The PD system of the present disclosure incudes an PD cycler having a housing. At least one and perhaps three or more reusable PD fluid lines extend from the housing. When not connected to PD fluid containers or bags, the reusable PD fluid lines can be connected to disinfection connectors supported and provided by the housing. The reusable PD fluid lines may for example extend from a front of the housing and connect to disinfection connectors also provided at the front of the housing for ready access to the PD fluid lines. The reusable PD fluid lines may be color coded and/or keyed to match a colored or keyed connector of the PD fluid container or bag. The containers or bags may hold different dextrose or glucose level PD fluids, such as 1.36% glucose PD fluid, 2.27% glucose PD fluid and/or a last bag of a different formulation of PD fluid, such as icodextrin. The PD fluids may contain a bicarbonate component.

Inside the housing, reusable tubing runs from each of the reusable PD fluid lines, through a PD fluid supply valve for each PD fluid line, to a PD fluid inline heater. In an embodiment, each of the valves of the PD cycler is an electrically actuated valve having a reusable valve body that occludes (e.g., when unpowered) or allows (e.g., when powered) PD fluid to flow through the body. The PD fluid inline heater is also electrically actuated in one embodiment and is, for example, a resistive heater having a reusable heater body that accepts PD fluid for heating. The inline heater in an embodiment is able to heat PD fluid from room temperature to body temperature, e.g., 37° C., at a flowrate of at least 200 milliliters ("ml")/minute. A temperature sensor is located adjacent to the heater, e.g., downstream from the heater to provide feedback for temperature control.

Reusable tubing runs from the outlet of the PD fluid inline heater to an airtrap in one embodiment. Any of the tubing inside the housing of the cycler may be metal, e.g., stainless steel, or plastic, e.g., polyvinylchloride ("PVC") or a non-PVC material, such as polyethylene ("PE"), polyurethane ("PU"), polyetheretherketone ("PEEK") or polycarbonate ("PC"). In an embodiment, one or more level sensor is located adjacent to the airtrap so that a desired level or range of levels of PD fluid is/are maintained in the airtrap. A fluid line valve is located along a reusable fluid line downstream from the airtrap in an embodiment. At least one gas line valve located along at least one gas line is provided and used as discussed herein. The airtrap may be closed upstream by PD fluid supply valves to drain the airtrap when dictated by the output of the level sensors.

A reusable PD fluid pump is located within the cycler housing and includes a reusable pump body that accepts PD fluid for pumping. That is, the pump does not require the PD fluid to flow within a disposable item, such as a tube or cassette. The PD fluid pump may be an electrically operated piston pump, which is inherently accurate so that a separate PD fluid volume measurement apparatus, such as a balance chamber or an apparatus using the ideal gas law, is not needed. The PD fluid pump may alternatively be an electrically operated, gear or centrifugal pump, which may operate with a separate PD fluid volume measurement apparatus.

The PD fluid pump is controllable to pump to and from the patient at or below a pressure limit by controlling a level of current to the PD fluid pump. A positive patient pressure limit may for example be one to five psig (e.g., two psig (14 kPa)). A negative patient pressure limit may for example be −1.0 psig to −3.0 psig (e.g., −1.3 psig (−9 kPa)). The PD fluid pump is bidirectional and continuous in one embodiment, such that a single pump may be provided.

The PD cycler of the PD system of the present disclosure includes a control unit having one or more processor and one or more memory that receives signals or outputs from pressure sensors, temperature sensors and possibly a conductivity sensor and that processes the signals or outputs as feedback. The control unit uses pressure feedback to control the PD fluid pump to run at safe patient pressure limits during treatment and safe system limits during disinfection. The control unit uses temperature feedback to control the PD fluid heater to heat the fresh PD fluid to, e.g., body temperature.

The control unit also opens and closes the PD fluid valves in combination with the PD fluid pump and heater to run a priming sequence, a patient fill sequence, a patient drain sequence, and a disinfection sequence after a PD treatment, wherein each of the at least one reusable PD fluid supply line is connected to one of the at least one disinfection connectors, and wherein the reusable patient line is connected to the reusable patient line connector. The disinfection sequence readies the PD cycler for the next treatment. In an embodiment, unused, fresh PD fluid is heated after the final drain and is used for disinfection.

The use of fresh PD fluid as a disinfection fluid, if it contains bicarbonate, likely leads to the formation of calcium carbonate in the disinfected flowpaths and flow components of the PD machine or cycler. The present system accordingly includes a source of an acid solution that is used during disinfection to prevent the formation of calcium carbonate. The acid solution may for example be a citric acid solution, e.g., fifty percent citric acid. An acid solution valve is located between the acid solution source and the disinfected flowpaths and flow components of the PD machine or cycler. In an embodiment, the control unit runs the PD fluid pump at a certain flowrate and pressure and opens the acid solution valve for a certain amount of time to meter a desired amount of citric acid solution into the disinfected flowpaths and flow components of the PD machine or cycler, wherein the determined time may be empirically determined and tested. In an alternative embodiment, the PD machine or cycler includes a conductivity cell, e.g., temperature compensated, which is used to provide feedback, such that the acid solution valve is opened until a desired conductivity is reached. In another alternative embodiment, a small, e.g., inherently accurate, acid solution metering pump under the control of the control unit is provided to meter a desired amount of acid solution into the disinfection loop of the PD machine or cycler.

If the PD solution used for disinfection includes a bicarbonate component, the acid solution will cause the bicarbonate to release carbon dioxide ("$CO_2$") gas into the disinfection loop. In the closed system, the released $CO_2$ gas causes the pressure in the disinfection loop to increase, which may affect the reliability of certain disinfected components. To prevent the pressure increase from reaching a point that could affect component reliability, it is contemplated for the control unit to monitor the pressure inside the disinfection loop during disinfection using the output from one or more pressure sensor. When the pressure reaches a certain threshold above the disinfection operating pressure (e.g., 10 kPa (1.5 psig)), the control unit first checks to make sure that the disinfection fluid (e.g., PD fluid mixed with acid solution) is below an upper threshold or level sensor in the airtrap of the PD machine. If so, the control unit in one embodiment causes at least one gas or vent valve located along at least one gas or vent line to open. The at least one gas line in an embodiment leads to a drain line connector. The pressurized $CO_2$ gas is then able to vent through the at least one gas line to and out of the drain line connector, e.g., through a flexible drain line leading from the drain line connector to a house drain (e.g., toilet or bathtub) or to a drain container.

In an alternative embodiment for removing $CO_2$ gas to drain, one or more PD fluid pump is used to pump the $CO_2$ gas to the drain line. The PD fluid pump may for example be the PD fluid pump that is used during treatment to pull effluent from the patient and to push same to drain.

In an alternative embodiment, after the control unit confirms that the disinfection fluid (e.g., PD fluid mixed with acid solution) is below the upper threshold or level sensor in the airtrap of the PD machine, the control unit causes valves leading to a container of a descaling agent, e.g., citric acid, to open such that pressurized $CO_2$ gas is able to flow into the container. The container may be flexible and expandable to accept the $CO_2$ gas or be rigid but oversized to accept the $CO_2$ gas. A priming sensor may be provided along the tube or line leading to the container of the descaling agent to ensure that $CO_2$ gas and not PD fluid flows to the container. The opening of the valves to allow $CO_2$ gas to flow into the descaling fluid container may be performed multiple times as needed over the course of a PD treatment. The $CO_2$ gas may be held within the container until the next treatment, at which time it is pumped to drain during a priming sequence using PD fluid.

In light of the disclosure set forth herein, and without limiting the disclosure in any way, in a first aspect of the present disclosure, which may be used with any other aspect, or portion thereof, a peritoneal dialysis ("PD") system includes a PD fluid pump; a disinfection loop including the PD fluid pump, the disinfection loop allowing PD fluid to be used for disinfecting the disinfection loop; an airtrap located along the disinfection loop; at least one gas valve located along at least one gas line leading to an upper portion of the airtrap; a pressure sensor positioned and arranged to sense PD fluid pressure in the disinfection loop during a disinfection sequence; and a control unit, the pressure sensor outputting to the control unit, the control unit configured to cause the at least one gas valve to open when the PD fluid pressure in the disinfection loop reaches or exceeds a threshold PD fluid pressure due to gas formation caused during the disinfection sequence.

In a second aspect of the present disclosure, which may be used with any other aspect, or portion thereof, the gas formation is caused by mixing the PD fluid with an acid solution.

In a third aspect of the present disclosure, which may be used with any other aspect, or portion thereof, the control unit is configured such that prior to causing the at least one gas valve to open, the control unit checks that a PD fluid level in the airtrap is not too high.

In a fourth aspect of the present disclosure, which may be used with any other aspect, or portion thereof, the PD system includes a drain line for draining used PD fluid during treatment, and wherein opening the at least one gas valve allows PD fluid pressure due to the gas formation to dissipate towards the drain line.

In a fifth aspect of the present disclosure, which may be used with any other aspect, or portion thereof, the control unit is further configured to at least one of (i) close at least one PD fluid valve located adjacent to the airtrap or (ii) stop the PD fluid pump when the PD fluid pressure reaches or exceeds the threshold PD fluid pressure.

In a sixth aspect of the present disclosure, which may be used with any other aspect, or portion thereof, the pressure sensor is located along one of the at least one gas line, which is in fluid communication with the disinfection loop, enabling the pressure sensor to sense PD fluid pressure during the disinfection sequence.

In a seventh aspect of the present disclosure, which may be used with any other aspect, or portion thereof, the pressure sensor or a second pressure sensor outputting to the control unit senses a PD fluid pressure dissipation after opening the at least one gas valve, the control unit further configured to close the at least one gas valve and continue the disinfection sequence upon receiving an output indicative of the PD fluid pressure dissipation.

In an eighth aspect of the present disclosure, which may be used with any other aspect, or portion thereof, the PD fluid system is configured such that opening of the at least one gas valve allows gas to dissipate from the upper portion of the airtrap through one of the at least one gas line towards drain.

In a ninth aspect of the present disclosure, which may be used with any other aspect, or portion thereof, the control unit is further configured to cause the at least one gas valve to open, or to remain open for an amount of time, based on or more of (i) gas volume, (ii) a time duration from the commencement of gas formation, and/or (iii) a number of times that the control unit has previously cause the at least one gas valve to open.

In a tenth aspect of the present disclosure, which may be used with any other aspect, or portion thereof, a peritoneal dialysis ("PD") system includes a PD fluid pump; a disinfection loop including the PD fluid pump, the disinfection loop allowing PD fluid to be used for disinfecting the disinfection loop; an acid solution source containing an acid for use during a disinfection sequence; a drain line positioned and arranged to drain used PD fluid during treatment; a gas line; at least one gas valve located along the gas line, the at least one gas valve enabling fluid communication between the gas line and the drain line; a pressure sensor positioned and arranged to sense PD fluid pressure in the disinfection loop during the disinfection sequence; and a control unit, the pressure sensor outputting to the control unit, the control unit configured to cause the at least one gas valve to open when the PD fluid pressure in the disinfection loop reaches or exceeds a threshold PD fluid pressure due to gas formed from mixing the PD fluid and the acid during the disinfection sequence, and wherein opening the at least one gas valve allows PD fluid pressure due to the gas formation to dissipate towards the drain line.

In an eleventh aspect of the present disclosure, which may be used with any other aspect, or portion thereof, the PD system includes a heater configured to heat the PD fluid and the acid during the disinfection sequence to a disinfection temperature.

In a twelfth aspect of the present disclosure, which may be used with any other aspect, or portion thereof, the PD fluid includes bicarbonate and the gas formed is carbon dioxide ("$CO_2$") gas.

In an thirteenth aspect of the present disclosure, which may be used with any other aspect, or portion thereof, the control unit is further configured to cause the at least one gas valve to open, or to remain open for an amount of time, based on or more of (i) gas volume, (ii) a time duration from the commencement of gas formation, and/or (iii) a number of times that the control unit has previously cause the at least one gas valve to open.

In an fourteenth aspect of the present disclosure, which may be used with any other aspect, or portion thereof, a peritoneal dialysis ("PD") system includes a PD fluid pump; a disinfection loop including the PD fluid pump, the disinfection loop allowing PD fluid to be used for disinfecting the disinfection loop; an airtrap located along the disinfection loop; at least one gas valve located along at least one gas line leading to an upper portion of the airtrap; a pressure sensor positioned and arranged to sense PD fluid pressure in the disinfection loop during a disinfection sequence; and a control unit, the pressure sensor outputting to the control unit, the control unit configured to cause the at least one gas valve to open and the PD fluid pump to pump an amount of gas from the airtrap when the PD fluid pressure in the disinfection loop reaches or exceeds a threshold PD fluid pressure due to gas formation caused during the disinfection sequence.

In a fifteenth aspect of the present disclosure, which may be used with any other aspect, or portion thereof, the PD system includes a patient line valve located along a patient line, and wherein the control unit causes the patient line valve to be open when the PD fluid pump pumps the amount of gas from the airtrap.

In a sixteenth aspect of the present disclosure, which may be used with any other aspect, or portion thereof, the PD system includes a drain line valve located along a drain line, and wherein the control unit causes the patient line valve to be closed and the drain line valve to be open after the PD fluid pump pumps the amount of gas from the airtrap so as to deliver the gas to the drain line.

In a seventeenth aspect of the present disclosure, which may be used with any other aspect, or portion thereof, a peritoneal dialysis ("PD") system includes a PD fluid pump; a disinfection loop including the PD fluid pump, the disinfection loop allowing PD fluid to be used for disinfecting the disinfection loop; an acid solution source containing an acid for use during a disinfection sequence; a line positioned and arranged to deliver acid to the disinfection loop; at least one valve located along the line, the at least one valve enabling fluid communication between the line and the disinfection loop; and a pressure sensor positioned and arranged to sense PD fluid pressure in the disinfection loop during the disinfection sequence; and a control unit, the pressure sensor outputting to the control unit, the control unit configured to cause the at least one gas valve to open when the PD fluid pressure in the disinfection loop reaches or exceeds a threshold PD fluid pressure due to gas formed from mixing the PD fluid and the acid during the disinfection sequence, and wherein opening the at least one gas valve allows PD fluid pressure due to the gas formation to dissipate towards the acid solution source.

In an eighteenth aspect of the present disclosure, which may be used with any other aspect, or portion thereof, the line extends from the acid solution source to an airtrap located along the disinfection loop.

In a nineteenth aspect of the present disclosure, which may be used with any other aspect, or portion thereof, the control unit is configured to cause the at least one gas valve to open when the PD fluid pressure in the disinfection loop reaches or exceeds a threshold PD fluid pressure and an upper level sensor within the airtrap does not detect PD fluid.

In a twentieth aspect of the present disclosure, which may be used with any other aspect, or portion thereof, the threshold PD fluid pressure is at or above an operating pressure used for the disinfection sequence.

In a twenty-first aspect of the present disclosure, which may be used with any other aspect, or portion thereof, the PD system includes a sensor located along the line, the sensor configured to sense between gas and PD fluid residing within the line.

In a twenty-second aspect of the present disclosure, which may be used with any other aspect, or portion thereof, the control unit is configured to cause the at least one gas valve to open when the PD fluid pressure in the disinfection loop reaches or exceeds a threshold PD fluid pressure and an output of the sensor indicates gas residing within the line.

In a twenty-third aspect of the present disclosure, which may be used with any other aspect, or portion thereof, the control unit is configured to cause the at least one gas valve to close when and an output of the sensor indicates PD fluid residing within the line.

In a twenty-fourth aspect of the present disclosure, which may be used with any other aspect, or portion thereof, the acid is citric acid, the PD fluid includes bicarbonate and the gas is carbon dioxide ("$CO_2$") gas.

In a twenty-fifth aspect of the present disclosure, which may be used with any other aspect, or portion thereof, a peritoneal dialysis ("PD") system includes a PD fluid pump; a disinfection loop including the PD fluid pump, the disinfection loop allowing PD fluid used for disinfecting the disinfection loop; and an acid solution source positioned and arranged to supply an acid solution to the disinfection loop during a disinfection sequence using the PD fluid.

In a twenty-sixth aspect of the present disclosure, which may be used with any other aspect, or portion thereof, the PD system includes an acid solution valve located between the disinfection loop and the acid solution source, the acid solution valve opened to allow the acid solution to be supplied to the disinfection loop during the disinfection sequence.

In a twenty-seventh aspect of the present disclosure, which may be used with any other aspect, or portion thereof, the PD system includes a control unit and a conductivity sensor outputting to the control unit, and wherein the control unit is configured to run the PD fluid pump and open the acid solution valve to allow the acid solution to be supplied to the disinfection loop during the disinfection sequence until the conductivity sensor output indicates that a desired amount of acid solution has been supplied.

In a twenty-eighth aspect of the present disclosure, which may be used with any other aspect, or portion thereof, the PD system includes an acid solution metering pump located between the disinfection loop and the acid solution source, the acid solution metering pump controlled to meter a desired amount of acid solution to the disinfection loop during the disinfection sequence.

In a twenty-ninth aspect of the present disclosure, which may be used with any other aspect, or portion thereof, the disinfection loop includes an airtrap and a pressure sensor positioned and arranged to sense PD fluid pressure during the disinfection sequence, the pressure sensor outputting to a control unit, the control unit configured to cause at least one gas valve located along at least one gas line leading to an upper portion of the airtrap to open when the PD fluid pressure reaches or exceeds a threshold PD fluid pressure due to gas formation caused by mixing the acid solution with the PD fluid.

In a thirtieth aspect of the present disclosure, which may be used with any other aspect, or portion thereof, the PD system includes a drain line for draining used PD fluid during treatment, and wherein opening the at least one gas valve allows PD fluid pressure due to the gas formation caused by mixing the acid solution with the PD fluid to dissipate towards the drain line.

In a thirty-first aspect of the present disclosure, which may be used with any other aspect, or portion thereof, the control unit is further configured to at least one of (i) cause at least one PD fluid valve located adjacent to the airtrap to close or (ii) cause the PD fluid pump to stop when the PD fluid pressure reaches or exceeds the threshold PD fluid pressure.

In a thirty-second aspect of the present disclosure, which may be used with any other aspect, or portion thereof, the pressure sensor is located along one of the at least one gas line, which is in fluid communication with the disinfection loop, enabling the pressure sensor to sense PD fluid pressure during the disinfection sequence.

In a thirty-third aspect of the present disclosure, which may be used with any other aspect, or portion thereof, the PD fluid used for disinfecting the disinfection loop is fresh PD fluid, and wherein the disinfection loop includes at least one reusable PD fluid supply line previously connected to a source of the fresh PD fluid.

In a thirty-fourth aspect of the present disclosure, which may be used with any other aspect, or portion thereof, the disinfection loop includes at least one of (i) a reusable patient line, or (ii) an inline heater, and wherein the PD fluid used for disinfecting the disinfection loop is heated by the inline heater.

In a thirty-fifth aspect of the present disclosure, which may be used with any other aspect, or portion thereof, any of the features, functionality and alternatives described in connection with any one or more of FIGS. 1 to 7 may be combined with any of the features, functionality and alternatives described in connection with any other of FIGS. 1 to 7.

It is accordingly an advantage of the present disclosure to provide a system for an automated peritoneal dialysis ("PD") cycler that helps to ensure that overpressurization does not occur during disinfection.

It is another advantage of the present disclosure to provide a system for an PD cycler that helps to ensure that overpressurization does not occur during disinfection, without requiring a vent to atmosphere, which may pose sterility issues over time.

It is a further advantage of the present disclosure to provide a system for an PD cycler that helps to prevent the build-up of precipitates during disinfection.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Overview

Figure 1:
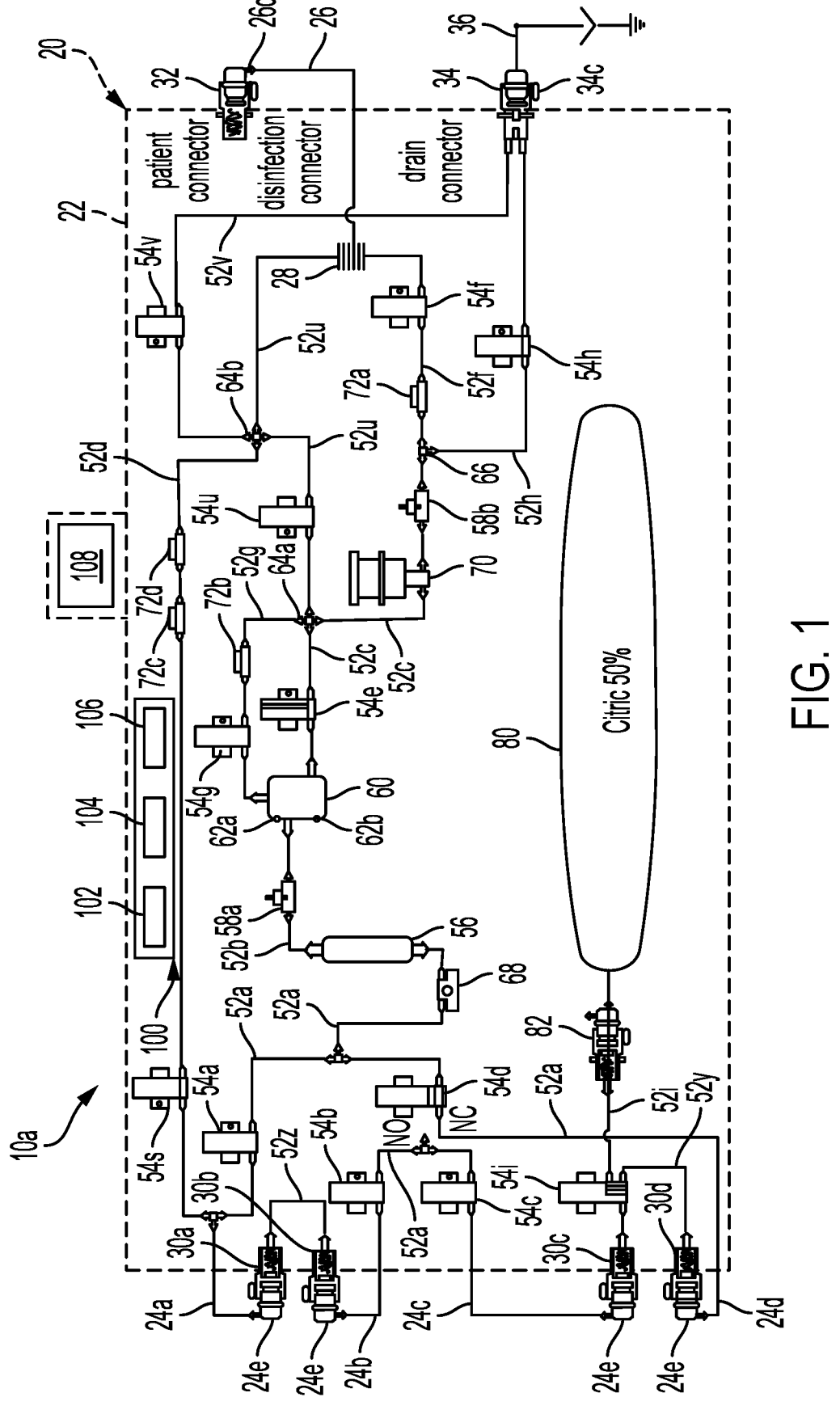
FIG. 1 is a schematic view of one embodiment of an automated peritoneal dialysis ("PD") system and associated disinfection product gas removal method of the present disclosure.

Referring now to the drawings and in particular to FIG. 1, automated peritoneal dialysis ("PD") system 10a and associated methodology of the present disclosure includes an PD machine or cycler 20. System 10a and cycler 20 attempt to eliminate disposable items as much as possible and instead provide the majority of its fluid carrying portions as reusable components, which are disinfected after treatment. Fluid lines within the machine or cycler are reused. In particular, FIG. 1 illustrates that cycler 20 includes a housing 22 from which reusable PD fluid supply lines 24a to 24d extend. FIG. 1 further illustrates that a reusable patient line 26 also extends from housing 22 of machine or cycler 20. Reusable patient line 26, which is typically longer than reusable PD fluid supply lines 24a to 24d, may be coiled or rolled up within the housing via a spool or hose reel 28 when reusable patient line 26 is not connected to a patient for treatment.

When not connected to PD fluid containers or bags, the reusable PD fluid supply lines 24a to 24d and patient line 26 can be connected to dedicated connectors supported and provided by the housing. The reusable PD fluid supply and patient lines may for example extend from a front of the housing and connect to connectors also provided at the front of the housing for ready access to the PD fluid and patient lines. In the illustrated embodiment, distal ends 24e of reusable PD fluid supply lines 24a to 24d releasably attach in a fluid-tight manner to disinfection connectors 30a to 30d, respectively, provided at housing 22. Distal end 26d of reusable patient line 26 releasably attaches in a fluid-tight manner to patient line connector 32 provided at housing 22 (or alternatively to a disinfection cap). Disinfection connectors 30a to 30d and patient line connector 32 may be configured to close or shut automatically when reusable PD fluid supply lines 24a to 24d and reusable patient line 26, respectively, are removed or not connected to the connectors.

FIG. 1 also illustrates that housing 22 provides a drain line connector 34, which may be releasably covered by a moveable, e.g., rotatable or slideable cover (not illustrated). Drain line connector 34 receives a disposable drain line 36 for treatment, which may run to a drain container or bag or to a house drain. Disposable drain line 36 is connected to drain line connector 34 during disinfection as discussed below.

Disposable PD fluid or solution containers or bags (not illustrated because system 10a is in a disinfection configuration with the containers or bags removed) are connected respectively to reusable PD fluid supply lines 24a to 24d. Distal ends 24e of reusable PD fluid supply lines 24a to 24d may be color coded and/or keyed to match a colored or keyed connector of a dedicated PD fluid container or bag. The containers or bags may hold the same or different dextrose or glucose level PD fluids, such as 1.36% glucose PD fluid, 2.27% glucose PD fluid, 3.86% glucose PD fluid, PD fluids containing bicarbonate, and/or a last bag of a different formulation of PD fluid, such as icodextrin.

It should be appreciated that any number of reusable PD fluid supply lines 24a to 24d and PD fluid containers or bags may be provided, including a single reusable PD fluid line and PD fluid container or more than one reusable PD fluid lines and PD fluid containers. In a further alternative embodiment, the PD fluid containers or bags are replaced by an online PD fluid generation source, which connects to and communicates fluidly with a single reusable PD fluid supply line.

Besides disposable drain line 36 (and associated container if used) and the disposable PD fluid containers or bags, it is contemplated that in one embodiment, the only other disposable component of system 10a is a disposable filter set (not illustrated) removably connected by the patient at the distal end 26d of reusable patient line 26 to provide a final stage of PD fluid filtration prior to delivery to the patient. In an embodiment, the disposable filter set is spliced between the distal end 26d of reusable patient line 26 and the patient's transfer set, which leads to an indwelling PD catheter inserted into the patient.

It is contemplated that any one, or more, or all of reusable PD fluid supply lines 24a to 24d, reusable patient line 26, disinfection connectors 30a to 30d, patient line connector 32, drain line connector 34, drain line 36, the PD fluid containers or bags and the patient line filter set be made of any one or more plastic, e.g., polyvinylchloride ("PVC") or a non-PVC material, such as polyethylene ("PE"), polyurethane ("PU"), polypropylene ("PP"), polyetheretherketone ("PEEK"), polycarbonate ("PC") or silicone.

FIG. 1 further illustrates that reusable supply tube 52a runs from each reusable PD fluid supply line 24a to 24d, through a PD fluid supply valve 54a to 54d, respectively, to a PD fluid inline heater 56. In an embodiment, each of the valves of the PD cycler 20, including PD fluid supply valves 54a to 54d, is an electrically actuated valve having a reusable valve body that occludes (e.g., when unpowered for fail safe operation) or allows (e.g., when powered) PD fluid to flow through the body. In the illustrated embodiment, valve 54d is a three-way valve having a normally open port for receiving PD fluid from reusable PD fluid supply line 24b or 24c and a normally closed port for receiving PD fluid from reusable PD fluid supply line 24d. PD fluid inline heater 56 is also electrically actuated in one embodiment and is, for example, a resistive heater having a reusable heater body that accepts PD fluid for treatment and disinfection heating. Inline heater 56 in an embodiment is able to heat PD fluid from room temperature or colder (e.g., if the PD fluid is stored in a cold environment) to body temperature, e.g., 37° C., at a flowrate of up to at least 200 milliliters ("ml")/minute.

A first temperature sensor 58a is located adjacent to heater 56, e.g., downstream from the heater to provide feedback for temperature control. If desired, a second temperature sensor (not illustrated) may be provided upstream from heater 56 to enable the incoming temperature of fresh PD fluid to be taken into account for the heating algorithm. A second temperature sensor 58b is illustrated just downstream from PD fluid pump 70, which is provided for example as a second check that fresh PD fluid exiting PD fluid pump 70 is at a desired temperature for treatment, e.g., body temperature or 37° C.

In the illustrated embodiment, a flow switch 68 is located just upstream from PD fluid inline heater 56. An output from flow switch 68 is used to make sure there is fresh PD fluid flow through inline heater 56. If the output (or lack thereof) from flow switch 68 indicates no or little fresh PD fluid flow, which could be harmful to inline heater 56 if powered, causes system 10a to halt power to inline heater 56 and to stop treatment or disinfection if needed while (i) attempting to find a remedy to the no or low flow situation or (ii) causing an audio, visual or audiovisual alarm or alert at user interface 108. It should be noted that cycler 20 of system 10a may employ additional or alternative hardware and/or software for ensuring that PD fluid is flowing when heater 56 is powered.

Reusable tube 52b runs from the outlet of PD fluid inline heater 56 to an airtrap 60 in the illustrated embodiment of FIG. 1. Any of the reusable tubing inside the housing of cycler 20, including reusable tubes 52a and 52b, may be made of metal, e.g., stainless steel or plastic, e.g., polyvinylchloride ("PVC") or a non-PVC material, such as polyethylene ("PE"), polyurethane ("PU"), polypropylene ("PP"), polyetheretherketone ("PEEK"), polycarbonate ("PC") or silicone. In an embodiment, one or more level sensor 62a and 62b is located adjacent airtrap 60 so that a desired level or range of levels of PD fluid is/are maintained in the airtrap. A fluid line valve 54e is located downstream from airtrap 60 in the illustrated embodiment and receives fresh, heated PD fluid from airtrap 60. A gas line valve 54g is located along a gas line 52g extending from a top of airtrap 60. Airtrap 60 may be closed upstream by PD fluid supply valves 54a to 54d to drain the airtrap when dictated by the output of level sensor 62a or 62b.

A reusable fluid line 52c and gas line 52g run between fluid line valve 54e and gas line valve 54g, respectively, and a PD fluid pump 70 located within housing 22 of cycler 20. PD fluid pump 70 includes a reusable pump body that accepts PD fluid for pumping. That is, pump 70 does not require the PD fluid to flow within a disposable item, such as a tube or cassette. The reusable pump body of pump 70 itself accepts the PD fluid. PD fluid pump 70 may be of a type, e.g., piston pump, which is inherently accurate so that a separate PD fluid volume measurement apparatus, such as a balance chamber or flowmeter, is not needed. PD fluid pump 70 may alternatively be a less accurate gear or centrifugal pump that does operate with a PD fluid volume measurement apparatus. PD fluid pump 70 is controllable to pump to and from the patient at or below a pressure limit by controlling a level of current to the PD fluid pump. A positive patient pressure limit may for example be one to five psig (e.g., two psig (14 kPa)). A negative patient pressure limit may for example be −1.0 psig to −3.0 psig (e.g., −1.3 psig (−9 kPa)). PD fluid pump 70 is also capable of supplying lower pressures if needed, e.g., for small children or babies. PD fluid pump 70 is bidirectional and continuous in one embodiment, such that a single pump may be provided.

FIG. 1 further illustrates that a fresh PD fluid patient line valve 54f is located in an embodiment along reusable fresh PD fluid patient tube or line 52f between downstream temperature sensor 58b and spool or hose reel 28. Fresh PD fluid patient tube or line 52f communicates fluidly with a fresh PD fluid lumen of dual lumen reusable patient line 26 in one embodiment. A used PD fluid patient line valve 54u is located in an embodiment along reusable used PD fluid patient tube or line 52u between PD fluid pump 70 (via cross 64a) and spool or hose reel 28. Used PD fluid patient tube or line 52u communicates fluidly with a used PD fluid lumen of dual lumen reusable patient line 26 in one embodiment. A drain line valve 54h is located along reusable drain tube or line 52h that extends from a tee 66 to drain line connector 34.

A first patient pressure sensor 72a is located along fresh PD fluid patient tube or line 52f between PD fluid pump 70 and spool or hose reel 28 to measure positive patient PD fluid pressure. A second patient pressure sensor 72b is located along gas line 52g to measure negative patient PD fluid pressure during a patient drain (note that gas line 52g may contain gas, PD fluid or a combination thereof, and that any gas is at the same negative pressure as used PD fluid via fluid communication at cross 64a). Third and fourth pressures sensor 72c and 72d are located along reusable disinfection tube or line 52d.

As discussed above, patient line connector 32 is located at PD cycler housing 22 and accepts dual lumen reusable patient line 26 during disinfection and generally while the patient is not undergoing treatment. Patient line connector 32 in one embodiment includes a sealed fluidic U-turn or 180 degree turn that allows disinfection fluid, e.g., heated PD fluid, to flow from one lumen of the dual lumen patient line to another lumen of the dual lumen patient line. Dual lumen reusable patient line 26 is therefore included in the disinfection loop. In an alternative embodiment, patient line connector 32 may be replaced by a disinfection cap that includes a sealed fluidic U-turn or 180 degree turn that allows disinfection fluid, e.g., heated PD fluid, to flow from one lumen of the dual lumen patient line to another lumen of the dual lumen patient line. The disinfection cap may be tethered to the end of reusable patient line 26 so that it is easily located when needed.

As further discussed above, drain line 36 is flexible and disposable in one embodiment and connects to drain line connector 34 extending from housing 22 of PD cycler 20 during treatment. After treatment, drain line 36 is left in place in one embodiment so that offgassing occurring during the disinfection sequence may be vented into drain line 36 towards the house or container drain. Drain line connector 34 receives internal, reusable drain tube or line 52h for delivering (i) used PD fluid to drain line 36 during a patient drain and (ii) air to drain line 36 during priming Drain line connector 34 also receives vent tube or line 52v for delivering gas, such as carbon dioxide ("$CO_2$") gas, to drain line 36 during disinfection as described in detail herein. A vent valve 54v is located along vent tube or line 52v.

A reusable disinfection tube or line 52d as illustrated in FIG. 1 extends to a second cross 64b along with vent tube or line 52v and used PD fluid patient tube or line 52u. Reusable disinfection tube or line 52d includes a disinfection valve 54s. As discussed in more detail herein, disinfection tube or line 52d handles disinfection fluid or fresh, heated PD fluid, vent tube or line 52v handles vented gas or $CO_2$, while used PD fluid patient tube or line 52u handles used PD fluid during treatment and is split during disinfection, wherein (i) the portion of used PD fluid patient tube or line 52u between first cross 64a and second cross 64b transfers $CO_2$ gas to vent tube or line 52v and (ii) the portion of used PD fluid patient tube or line 52u between second cross 64b and spool or hose reel 28 transfers disinfection or fresh PD fluid to or from disinfection tube or line 52d.

FIG. 1 also illustrates that an acid solution source 80 is connected to an acid solution connector 82. An acid solution line 52i extends from solution connector 82 to a three-way acid solution valve 54i, e.g., to the normally open port of valve 54i. Three-way valve 54i also controls a bypass line 52y between disinfection connectors 30c and 30d, which is used during disinfection. A similar bypass line 52z is provided between disinfection connectors 30a and 30b. Acid solution source 80 holds an acid solution that is used during disinfection as described herein. The acid solution may for example be a citric acid solution, e.g., fifty percent citric acid. It should be appreciated that acid solution source 80 may be located virtually anywhere along the disinfection loop, e.g., at bypass line 52z or along disinfection tube or line 52d, etc. System 10b of FIG. 4 discussed below illustrates one preferred location for acid solution source 80.

FIG. 1 further illustrates that PD cycler 20 of system 10a of the present disclosure includes a control unit 100 having one or more processor 102 and one or more memory 104 that receive, store and process signals or outputs from the pressure sensors 72a to 72d, temperature sensors 58a and 58b, flow switch 68 and possibly a conductivity sensor (not illustrated). Control unit 100 uses pressure feedback from pressure sensors 72a and 72b to control PD fluid pump 70 to pump fresh and used PD at safe patient and system pressure limits. Control unit 100 uses temperature feedback from temperature sensor 58a to control inline PD fluid heater 56 to heat the fresh PD fluid to, e.g., body temperature or 37° C. Control unit 100 uses flow switch feedback from flow switch 68 to determine whether to power PD fluid inline heater 56.

Control unit 100 also opens and closes PD fluid valves 54a to 54i, 54s, 54u and 54v in combination with the operation of PD fluid pump 70 and heater 56 to run a priming sequence, multiple patient fill sequences, multiple patient drain sequences, and a disinfection sequence after a PD treatment. In the disinfection sequence, each reusable PD fluid supply line 24a to 24d is connected to a respective disinfection connector 30*a* to 30*d,* respectively and reusable patient line 26 is connected to reusable patient line connector 32. The disinfection sequence readies PD cycler 20 for the next treatment. In an embodiment, remaining fresh PD fluid is heated after the final patient drain and is used as the disinfection fluid for disinfection.

Control unit 100 as illustrated in FIG. 1 also includes a video controller 106 that interfaces with a user interface 108, which may include a display screen operating with a touch-screen and/or one or more electromechanical button, such as a membrane switch. User interface 108 may also include one or more speaker for outputting alarms, alerts and/or voice guidance commands. User interface 108 may be provided with cycler 20 as illustrated in FIG. 1 and/or be a remote user interface operating with control unit 100. Control unit 100 may also include a transceiver (not illustrated) and a wired or wireless connection to a network, e.g., the internet, for sending treatment data to and receiving prescription instructions from a doctor's or clinician's server interfacing with a doctor's or clinician's computer.

Figure 2:
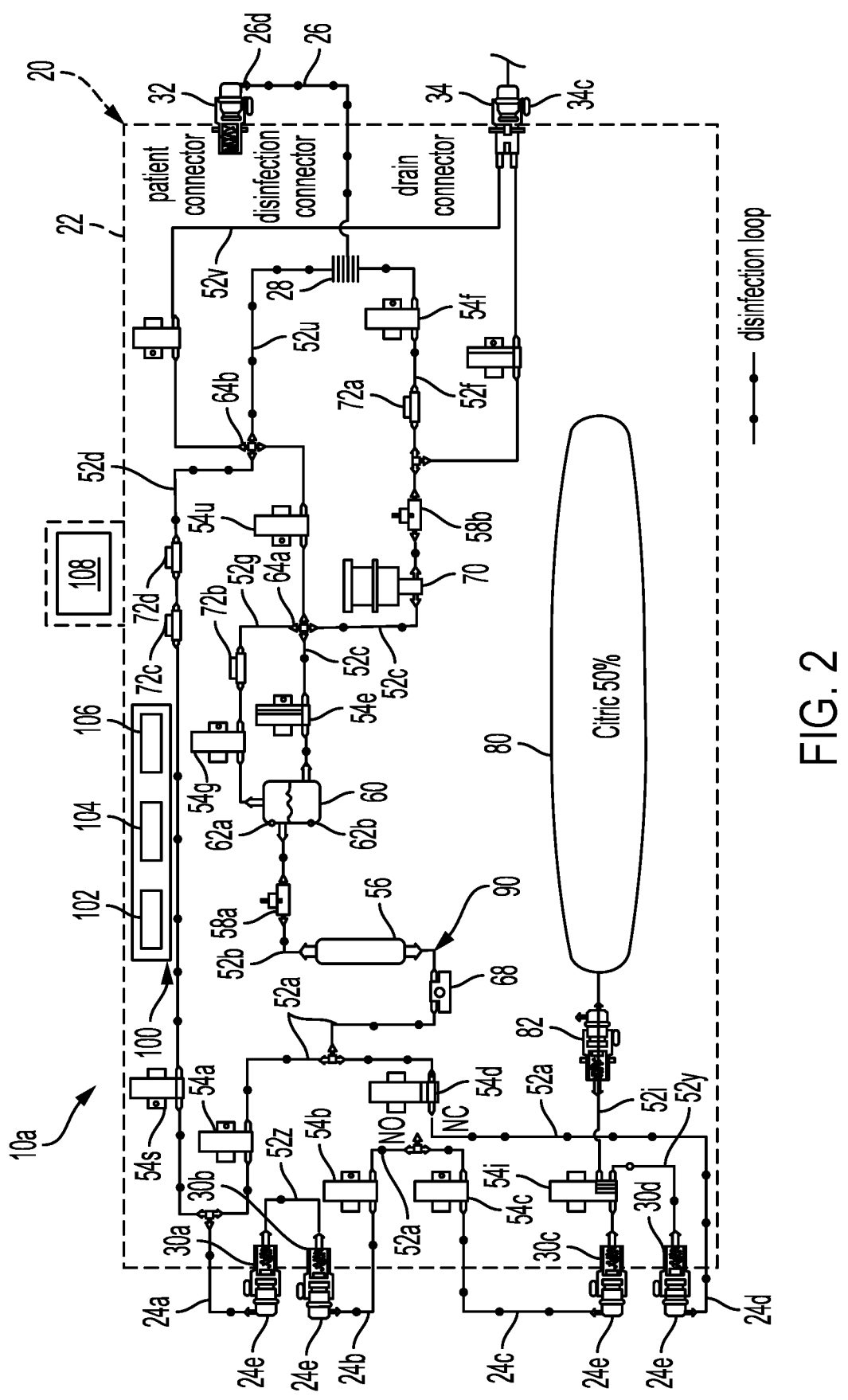
FIG. 2 is the schematic view of FIG. 1 showing one example disinfection flowpath or disinfection loop for the PD system of the present disclosure.

Referring now to FIG. 2, a disinfection loop 90 including the disinfected lines and components is highlighted. All other lines and components described in connection with FIG. 1 are provided but are in general not numbered in FIG. 2 for ease of illustration. Disinfection loop 90 includes (lines with dots, introduced generally counterclockwise) patient line connector 32 (including its U-turn or 180 degree turn), both lumens of reusable dual lumen patient line 26, the portion of used PD fluid patient tube or line 52*u* between spool or hose reel 28 and second cross 64*b,* reusable disinfection tube or line 52*d,* reusable PD fluid supply lines 24*a* to 24*d,* bypass lines 52*y,* 52*z,* and reusable tubes or lines 52*a* to 52*c* and 52*f.* Disinfection loop 90 also includes the insides of all flow components and sensors located along the above-listed lines.

Control unit 100 may sequence certain of the valves along disinfection loop 90 during disinfection. For example, PD fluid supply valve 54*a* may be sequenced open and closed during disinfection to allow disinfection fluid to flow through supply valve 54*a* or be forced completely through reusable PD fluid supply line 24*a.* Control unit 100 may also cause PD fluid pump 70 to run sequentially in forward and reverse states during disinfection, so that disinfection fluid may flow clockwise and counterclockwise through disinfection loop 90. Control unit 100 also causes inline heater 56 to heat the disinfection fluid, e.g., fresh PD fluid, to a desired disinfection temperature, such as 70° C. to 90° C.

Delivering Disinfection Product Gas to Drain

The use of fresh PD fluid as a disinfection fluid, if it contains bicarbonate, likely leads to the formation of calcium carbonate in the disinfected flowpaths and flow components of disinfection loop 90 of PD machine or cycler 20. Acid from acid solution source 80 is provided accordingly during disinfection to prevent the formation of calcium carbonate. In an embodiment, control unit 100 causes PD fluid pump 70 to run at a certain flowrate and pressure and opens the acid solution valve 54*i* for a certain amount of time to meter a desired amount of citric (or other) acid solution into the disinfected flowpaths and flow components of disinfection loop 90, wherein the determined time may be empirically determined and tested. In an alternative embodiment, PD machine or cycler 20 includes a conductivity cell, e.g., temperature compensated (not illustrated but could be located anywhere along the disinfection loop, e.g., along reusable disinfection tube or line 52*d*), which is used to provide feedback to control unit 100, such that acid solution valve 54*i* is opened until a desired conductivity is reached in disinfection loop 90. In another alternative embodiment, a small, e.g., inherently accurate, acid solution metering pump (not illustrated) under the control of control unit 100 is provided to meter a desired amount of acid (e.g., citric) solution into the disinfection loop 90.

If the heated PD solution used for disinfection includes a bicarbonate component, the acid solution will cause the bicarbonate to release $CO_2$ gas into disinfection loop 90. In the closed disinfection loop 90, the released $CO_2$ gas causes the pressure in the disinfection loop to increase, which may promote internal leakage and affect the reliability of certain disinfected components located along the loop, such as PD fluid pump 70.

In FIG. 2, to prevent the pressure increase due to gas or $CO_2$ formation from reaching a point that could affect component reliability, it is contemplated for control unit 100 of system 10*a* to monitor the pressure inside disinfection loop 90 during disinfection using the output from one or more pressure sensor, such as any one or more of pressure sensors 72*a* to 72*d* (pressure sensor 72*b* senses disinfection pressure via fluid communication with first cross 64*a*). When the pressure reaches a certain threshold above a typical disinfection operating pressure, which typical operating pressure may for example be 10 kPa (1.5 psig), control unit 100 in one embodiment first checks to make sure that the disinfection fluid (e.g., heated fresh PD fluid mixed with acid solution) is below an upper threshold in airtrap 60 of PD machine or cycler 20. Here, control unit 100 may check to make sure that the disinfection fluid has not reached upper level sensor 62*a.* Control unit 100 makes this check to protect against PD fluid entering gas line 52*g.* An example threshold pressure above an operating pressure of, for example, 10 kPa (1.5 psig) may be 20 kPa (2.9 psig). That is, control unit 100 in one example looks for the overpressure, e.g., as measured at pressure sensor 72*b,* to reach 20 kPa (2.9 psig), which is about twice as much as the specified operating pressure.

Figure 3:
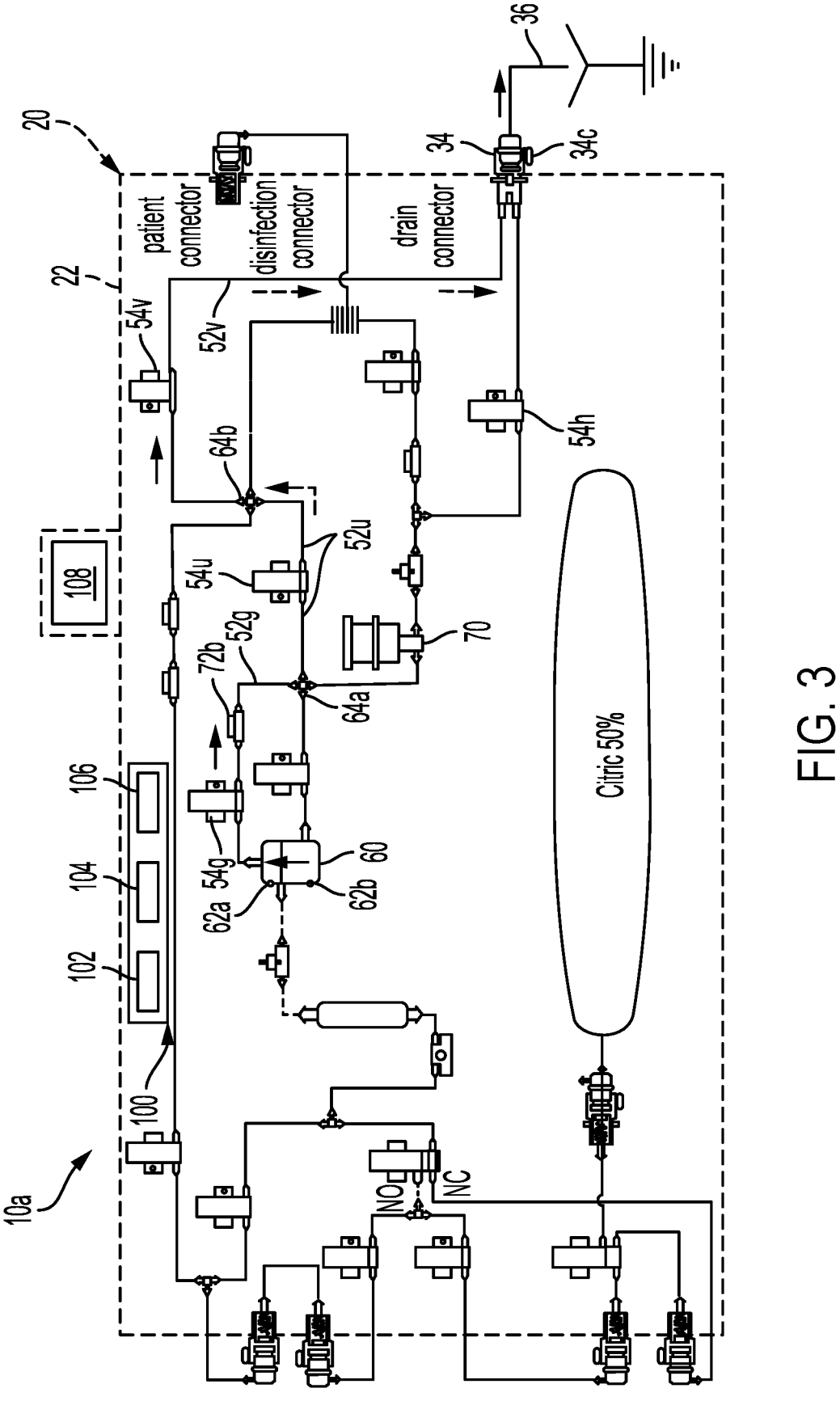
FIG. 3 is a schematic view of FIG. 1 showing one example release pressure flowpath for the PD system of the present disclosure.

Control unit 100, upon determining an overpressure and determining that the fluid level in airtrap 60 is not too high, causes disinfection valve 54*e* and any open valves 54*a* to 54*d* upstream of airtrap 60 to close to fluidically isolate the airtrap. Control unit 100 also causes PD fluid pump 70 to stop pumping disinfection fluid. Control unit 100 as illustrated in FIG. 3 further causes (i) gas line valve 54*g,* (ii) used PD fluid patient line valve 54*u,* and (iii) vent valve 54*v* to open to allow pressurized $CO_2$ gas to depressurize and flow from the top of airtrap 60 along the lines marked by arrows in FIG. 3 to drain line 36 via drain line connector 34. The pathway for depressurizing the $CO_2$ gas in the illustrated embodiment includes gas line 52*g,* the portion of used PD fluid patient tube or line 52*u* between crosses 64*a* and 64*b,* vent tube or line 52*v,* and drain line 36.

Once the $CO_2$ gas has been properly depressurized, e.g., to atmospheric pressure or zero kPa or perhaps to the typical disinfection operating pressure, such as 10 kPa (1.5 psig), as sensed at pressure sensor 72*b* outputting to control unit 100, the control unit causes (i) gas line valve 54*g,* (ii) used PD fluid patient line valve 54*u,* and (iii) vent valve 54*v* to close, and causes disinfection fluid valve 54*e* and any desired one or more upstream valve 54*a* to 54*d* to open, and actuates PD fluid pump 70 and inline heater 56 to continue disinfection. The depressurization sequence just described is repeated as many times as necessary prior to (e.g., while the disinfection fluid, e.g., PD fluid, is being heated for disinfection) and possibly during the course of the disinfection of disinfection loop 90. In one example, flexible drain line 36 is left in place while the disinfection fluid is being heated for disinfection, wherein the depressurization sequence occurs one or more time with drain line 36 in place to accept the removed $CO_2$ gas. When the disinfection fluid has been heated to the disinfection temperature, user interface 108 audibly, visually or audiovisually prompts the patient or user to then remove drain line 36 from drain line connector 34, which is then capped via drain line cap 34c to fluidically close disinfection loop 90 for the disinfection sequence.

The above depressurization sequence for removing $CO_2$ gas to drain line 36 is described as being triggered via an overpressure due to the formation of $CO_2$ gas. It is also stated that the depressurization sequence may be performed one or more time. In various embodiments, (i) the triggering of the depressurization sequence and (ii) the total amount of time needed to properly dissipate the $CO_2$ gas pressure may be a function of, and depend upon, any one or more of: (a) sensed pressure in disinfection loop 90, (b) an amount of time that has passed since the start of $CO_2$ gas production or from the end of a prior depressurization sequence, (c) a volume of $CO_2$ gas to be dissipated (e.g., calculated by control unit 100 knowing citric (or other) acid concentration and disinfection fluid temperature), and/or (d) a number of prior depressurization sequences that have already taken place.

It should be appreciated that the above-described depressurization sequence does not require a separate relief valve or hydrophobic air vent (but could use such a valve and/or vent if desired), which could present sterility issues. Any pathogens in the above depressurization sequence are forced to travel all the way up flexible drain line 36 and are isolated during disinfection via closed vent valve 54v and closed drain line valve 54h.

In an alternative depressurization sequence that similarly does not require a separate relief valve or hydrophobic air vent, control unit 100 of PD machine or cycler 20 instead causes one or more PD fluid pump, such as PD fluid pump 70, to pump disinfection gas or $CO_2$ to drain line 36. Here, control unit 100 may cause disinfection fluid valve 54e to be closed and gas line valve 54g to be opened so that PD fluid pump 70 may pull disinfection gas or $CO_2$ from the top of air trap 60 and push same to drain. To pull disinfection gas or $CO_2$ from the top of air trap 60, control unit 100, with patient line valve 54f open and drain line valve 54h closed, may cause PD fluid pump 70 to pull a volume of disinfection gas or $CO_2$ from air trap 60 equal to the inner tubular volume between the top of air trap 60 and tee 66 along gas line 52g, and then cause PD fluid patient line valve 54f to be closed and drain line valve 54h to be opened to allow PD fluid pump 70 to pump the removed volume of disinfection gas or $CO_2$ gas to drain. Any one or more triggering and/or timing factor (a) to (d) described above may also be used for any disinfection sequence involving the use of PD fluid pump 70.

Figure 4:
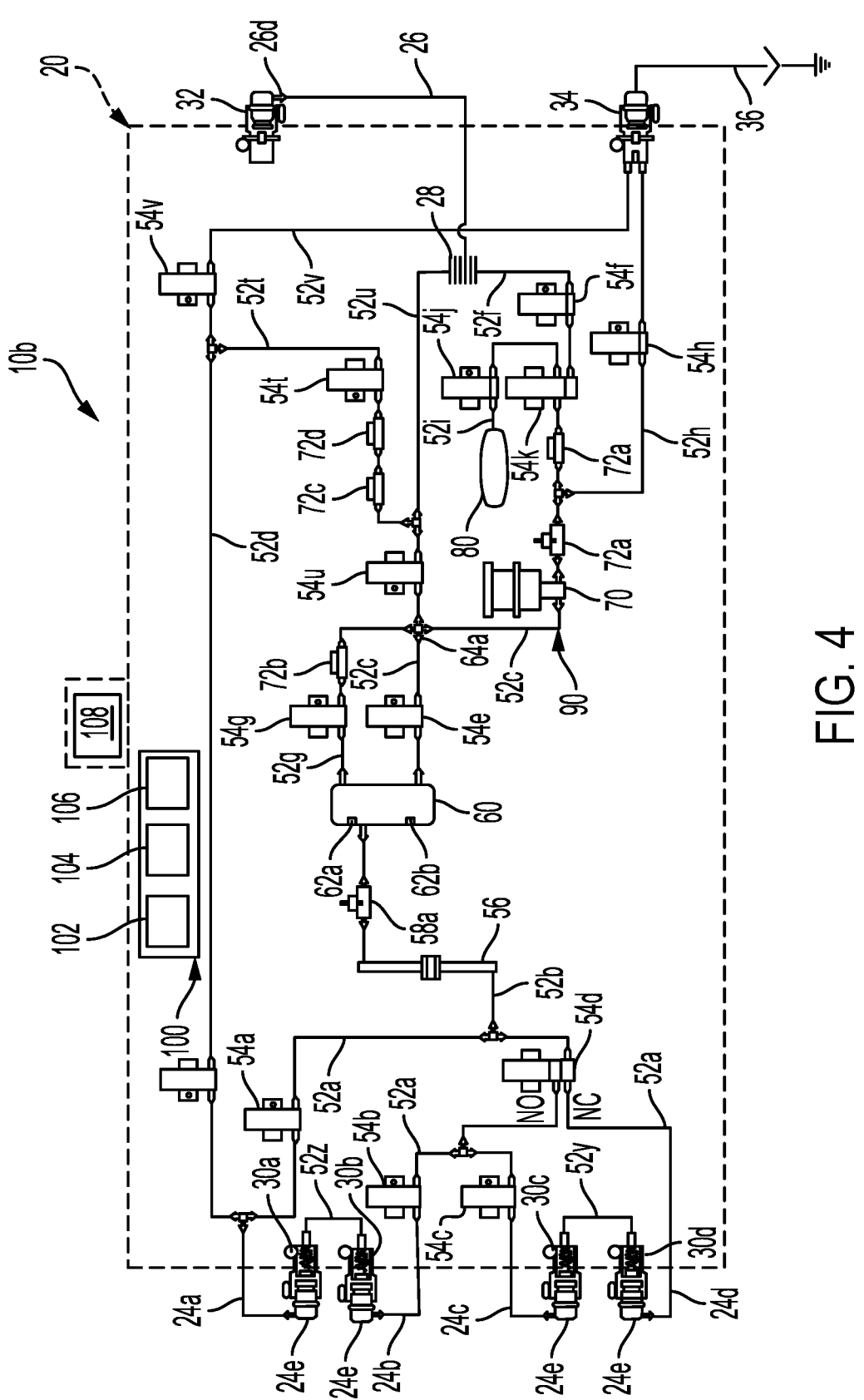
FIG. 4 is a schematic view of another embodiment of an automated peritoneal dialysis ("PD") system and associated disinfection product gas removal method of the present disclosure, illustrating one preferred location for acid solution source.

FIG. 4 illustrates an alternative PD system 10b for removing disinfection gas or $CO_2$ gas to drain. PD system 10b includes many of the same components as PD system 10a, including disinfection loop 90, which are numbered the same and include all structure, functionality and alternatives discussed above for those components. One primary difference with FIG. 4 is that acid solution source 80 is provided in one preferred location downstream from PD fluid pump 70 along the fresh PD fluid portion of disinfection loop 90. In an embodiment, PD fluid pump 70 is used to pump $CO_2$ gas to removable drain line 36. Using PD fluid pump 70 helps to minimize the amount of PD fluid needed to flush the $CO_2$ gas. Locating acid solution source 80 downstream from PD fluid pump 70 as illustrated in FIG. 4 makes it impossible to pump $CO_2$ gas to the patient during treatment (with PD fluid pump 70 pumping in a forward delivery direction). Also, locating two valves 54j (two-way valve) and 54k (three-way valve) between acid solution source 80 and fresh patient tubing or line 52f provides redundancy in preventing (i) acid from being delivered to the patient and (ii) PD fluid from being pumped into acid solution source 80, diluting the acid solution. System 10b also includes an additional recirculation line 52t having a recirculation valve 54t under control of control unit 100.

Moreover, the dosing or amount of the acid (e.g., citric acid) delivered at the start of the disinfection sequence is improved with system 10b of FIG. 4. Here, before system 10b introduces the dose of acid, the system adjusts the pressure at acid solution source 80 to be either atmospheric or to be the last known pressure recorded at acid solution source 80. To use the last known pressure, during dosing of the acid, PD fluid pump 70 is run in reverse a set amount of strokes corresponding to a dose/stroke volume to withdraw the prescribed does of acid into disinfection loop 90. At the end of the acid dosing, control unit 100 records the pressure measured at pressure sensor 72a. That pressure is then stored as the beginning of dosing pressure at acid solution source 80, which is used during the next disinfection sequence to improve acid dose accuracy. Such pressure control may be applied to any embodiment for any system 10a to 10c described herein.

Figure 5:
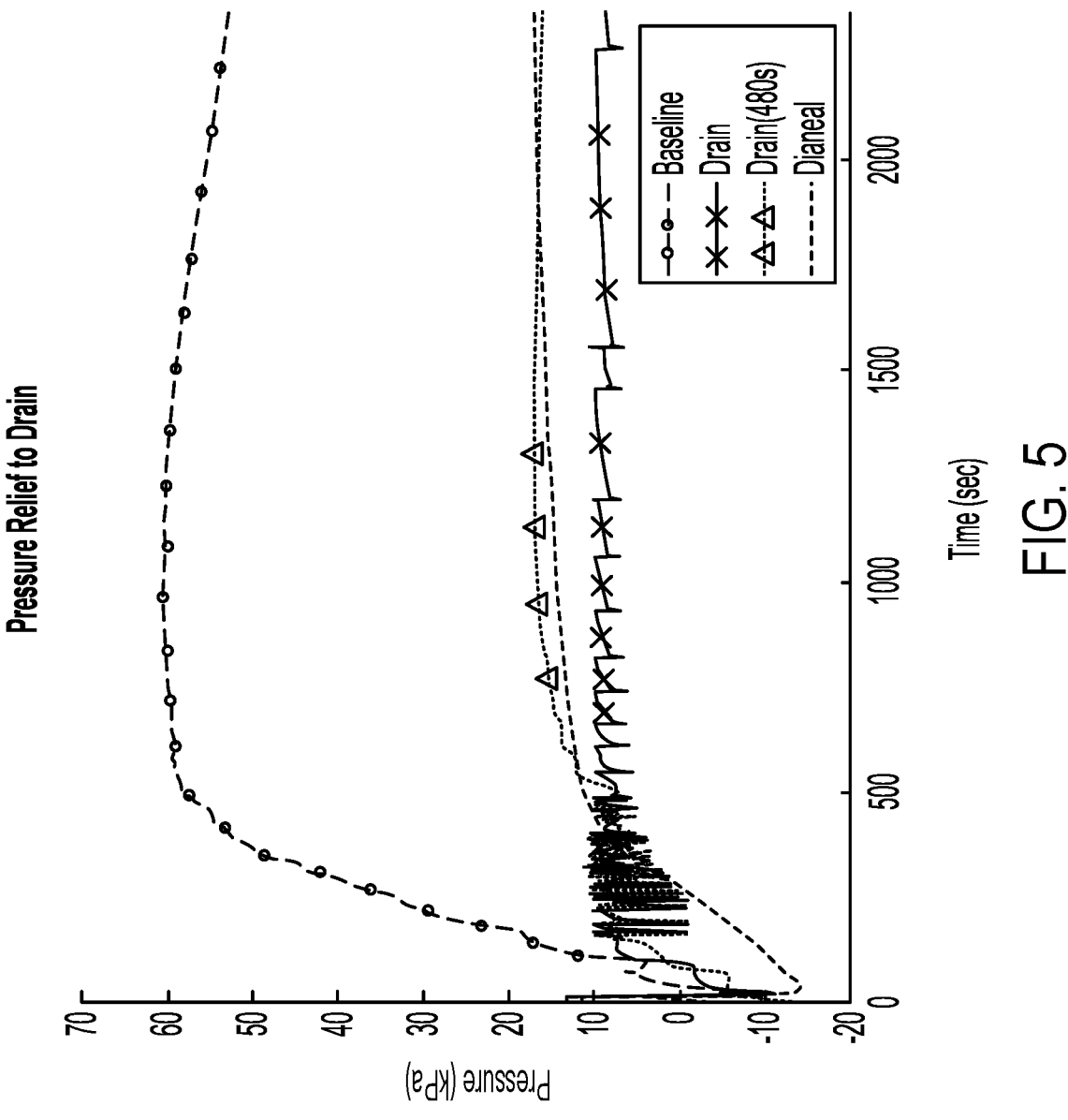
FIG. 5 is a plot versus time showing pressure relief examples using the system as associated methodology of the PD system of FIGS. 1 to 4.

FIG. 5 illustrates example outputs for the above-described depressurization sequence. The top line (dotted) is a baseline showing pressures that are present from offgassed $CO_2$ when bicarbonate PD fluid is used and the depressurization sequence of system 10a is not performed. The Δ-line and x-line are examples for PD fluids containing bicarbonate (e.g., Physioneal® PD fluid marketed by the assignee of the present disclosure), which have been combined with an acid solution, e.g., citric acid, leading to the byproduct production of $CO_2$ gas. Here, pressurized $CO_2$ gas is released in the manner described above upon the pressure reaching or surpassing a threshold pressure. In the tests performed leading to the plot of FIG. 5, the threshold pressure is taken as 10 kPa (1.5 psig). However, 10 kPa (1.5 psig) is likely to be in the operating pressure range during disinfection for system 10, while the threshold pressure for when to trigger the release of pressure may be significantly higher. As illustrated in FIG. 5, the pressure increase due to offgassed $CO_2$ is strongly curtailed due to the depressurization in the Δ-line and x-line versus the non-depressurized dotted line.

The unmarked line is for a particular PD fluid marketed by the assignee of the present disclosure, namely, Dianeal® PD fluid, which contains no bicarbonate and therefore does not need to be infused with a descaling fluid, such as citric acid during disinfection. The unmarked non-bicarbonate line may therefore be taken as a model line for the Δ-line and x-line. The difference between the bicarbonate Δ-line and the x-line is that with the x-line, the patient removes disposable drain line 36 and caps drain line connector 34 with a drain line cap 34c (FIGS. 1 to 3) at time t0 or the beginning of the test for the x-line. With the Δ-line, the patient instead waits for a specified period, 480 seconds in the example of FIG. 5, to remove disposable drain line 36 and cap drain line connector 34 with a drain line cap 34c (FIGS. 1 to 3). During the waiting period or while the disinfection sequence is running, disinfection fluid is heated to the disinfection temperature, creating the byproduct disinfection or $CO_2$ gas. With the Δ-line, $CO_2$ gas is only vented while disposable drain line 36 is present, e.g., during the 480 seconds. After disposable drain line 36 is removed, no additional CO$_2$ gas is vented from the system. The venting period as illustrated however is long enough to keep the Δ-line pressure well below the dotted baseline pressure. The x-line is a reference line in which disposable drain line 36 is left in place over the whole test so that CO$_2$ gas can be vented over the whole test. As illustrated, both the Δ-line and the x-line generally follow the non-bicarbonate line and have pressures well below that of the dotted baseline, which shows pressures that are present when bicarbonate PD fluid is used and the depressurization sequence of system 10a is not performed. Also, the Δ-line pressure does not increase appreciably over the x-line pressure.

Delivering Disinfection Product Gas to Acid Solution Source

Figure 6:
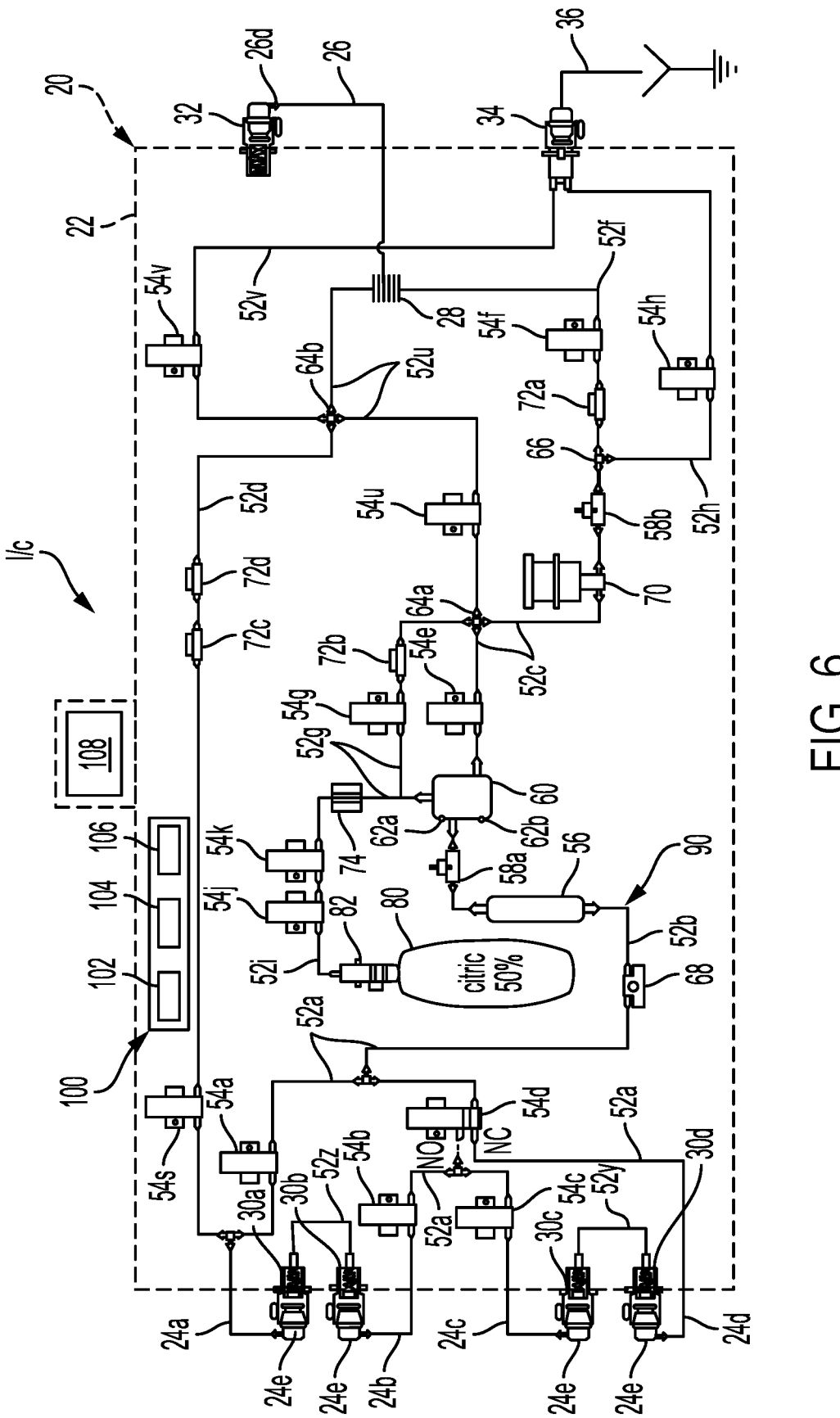
FIG. 6 is a schematic view of an alternative embodiment of an automated peritoneal dialysis ("PD") system and associated disinfection product gas removal method of the present disclosure.

FIG. 6 illustrates a further alternative PD system 10c. PD system 10c includes many of the same components as PD system 10a, which are numbered the same and include all structure, functionality and alternatives discussed above for those components. In particular, system 10c includes cycler 20 and control unit 100 having one or more processor 102, one or more memory 104, video controller 106 and user interface 108. System 10c includes inline dialysis fluid heater 56, reusable lines or tubes 52a and 52b, PD fluid supply valves 54a to 54d, air trap 60 operating with respective upper and lower level sensors 62a and 62b, disinfection fluid valve 54e, gas line valve 54g located along a gas line 52g, reusable line or tube 52c leading to dialysis fluid pump 70, temperature sensors 58a and 58b, pressure sensors 72a, 72b, 72c and 72d, reusable fresh and used patient tubing or lines 52f and 52u, respectively, hose reel 28, dual lumen reusable patient line 26, reusable drain tube or line 52h extending to drain line connector 34 and having a drain line valve 54h, vent line 52v having a vent valve 54v, and reusable recirculation or disinfection tube or line 52d operating with respective disinfection valve 54s. A third recirculation or disinfection tube or line 52y extends between disinfection connectors 30c and 30d for use during disinfection. A fourth recirculation or disinfection tube or line 52z extends between disinfection connectors 30a and 30b for use during disinfection. The above lines and components form a disinfection loop 90, which is disinfected after treatment. Each of pump 70, heater 56, the valves and sensors is controlled by and/or outputs to control unit 100.

One primary difference with system 10c is that acid solution source 80, acid solution connector 82 and acid solution line 52i are moved from the position shown in FIGS. 1 to 3, so that acid solution line 52i extends instead to gas line 52g extending from a top of airtrap 60. Recirculation or disinfection tube or line 52y extends accordingly directly between disinfection connectors 30c and 30d instead of to three-way acid solution valve 54i in system 10a, which is removed in system 10c. Two two-way acid solution valves 54j and 54k are provided along acid solution line 52i, adding redundancy to ensure that an acid solution, such as citric acid, cannot leak or otherwise flow into the treatment pathway (e.g., into lines 52c, 52f and the fresh PD fluid lumen of dual lumen reusable patient line 26) during treatment.

Another addition found in system 10c is a priming sensor 74 outputting to control unit 100, wherein priming sensor 74 in the illustrated embodiment is positioned along gas line 52g but may alternatively be located along acid solution line 52i. Priming sensor 74 is configured to detect whether CO$_2$ gas versus acid, such as citric acid, or PD fluid (mixed with an acid) is located in, e.g., flowing within, gas line 52g and/or acid solution line 52i. Priming sensor 74 in various embodiments is an ultrasonic, optical, inductive, capacitive or magnetic sensor outputting to control unit 100.

Testing has shown that using citric acid as a descaling agent and heating the disinfecting PD fluid to 85° C. will for example create 110 ml of CO$_2$ gas when 2.1 ml of 50% (by weight) of citric acid is added to 300 ml (approximate volume of disinfection loop 90) of a bicarbonate containing PD fluid. An advantage of the location of acid solution source 80, acid solution connector 82 and acid solution line 52i in system 10c is that a disinfection product gas, such as carbon dioxide ("CO$_2$"), may be delivered to and held within the empty space of acid solution source 80. The container for acid solution source 80 is in one embodiment flexible, e.g., a polymer bag made of any of the materials discussed herein, which may expand upon receiving CO$_2$ gas and contract when CO$_2$ gas is removed from the bag.

During the teardown of system 10c after treatment, the patient or user connects distal end 26d of reusable patient line 26 to patient line connector 32 provided at housing 22, connects distal ends 24e of reusable PD fluid supply lines 24a to 24d to disinfection connectors 30a to 30d (as illustrated in FIG. 6), and removes disposable drain line 36, so that the moveable, e.g., rotatable or slideable, drain connector cover sealingly closes over drain line connector 34. Control unit 100 then causes valves 54e, 54j, 54k, 54f and 54s to be energized open, and PD fluid pump 70 to pull a desired amount of descaling fluid, e.g., 50% (by weight) citric acid, from acid solution source 80 and to deliver same to disinfection loop 90. Control unit 100 also reads the output from priming sensor 74 to confirm that citric acid has been injected into the PD fluid over a commanded number of strokes of PD fluid pump 70.

Control unit 100 next causes valves 54e, 54f, 54s, 54b and 54c to be energized open, PD fluid heater 56 to heat the PD fluid mixed with citric acid to a desired disinfection temperature, e.g., 85° C., and for PD fluid pump 70 to circulate the heated PD fluid around disinfection loop 90, e.g., in a timed manner, so that a proper amount of disinfection occurs. Control unit 100 may toggle any desired valve and reverse the flow direction of PD fluid pump 70 one or more time during the disinfection sequence.

During and perhaps for some time before and/or after the disinfection of disinfection loop 90, control unit 100 is able to enter a pressure release mode. In one embodiment, control unit 100 enters the pressure release mode when a pressure or pressures measured by one or more pressure sensor 72a to 72d located along disinfection loop 90 reach(es) or achieve(s) a threshold pressure, e.g., 10 kPa (1.5 psig)) or some delta pressure above a disinfection operating pressure as discussed herein. Control unit 100 may also read the output of upper level sensor 62a to ensure that the PD fluid level within airtrap 60 is below upper level sensor 62a. Control unit 100 then energizes open citric acid valves 54j and 54k to allow pressurized CO$_2$ gas to flow into the container of acid solution source 80. During this time, control unit 100 also looks to the output of priming sensor 74 to confirm that gas and not fluid is present and flowing. If fluid is detected, control unit 100 causes citric acid valves 54j and 54k to close. When the pressure(s) measured by one or more pressure sensor(s) 72a to 72d fall(s) to or below the threshold pressure, e.g., 10 kPa (1.5 psig)), control unit 100 causes citric acid valves 54j and 54k to close, preventing PD fluid from flowing into the container of acid solution source 80. Also, in one embodiment if the output from upper level sensor 62*a* to control unit 100 indicates that PD fluid mixed with citric acid has reached upper level sensor 62*a*, control unit 100 causes citric acid valves 54*j* and 54*k* to close. Control unit 100 is configured in one embodiment to enter the pressure release mode as many times as needed during (and possible slightly before and/or after) the disinfection sequence.

After the disinfection sequence, control unit 100 no longer monitors the pressure(s) measured by one or more pressure sensor(s) 72*a* to 72*d* for a disinfection product gas overpressure. It is contemplated to allow $CO_2$ gas to remain within the container of acid solution source 80 until the next treatment at which time a new disposable drain line 36 is connected to drain line connector 34. Control unit 100 causes citric acid valves 54*j* and 54*k*, valve 54*g* and drain valve 54*h* to open and PD fluid pump 70 to pull $CO_2$ gas from the container of acid solution source 80 and push same to or towards drain line 36. Control unit 100 monitors the output of priming sensor 74 to confirm that gas and not fluid is present and flowing during the removal of $CO_2$ gas from the container of acid solution source 80. The output priming sensor 74 (sensing citric or other acid) and/or of one or more pressure sensor, such as pressure sensor 72*b*, may be monitored by control unit 100 to know when to stop PD fluid pump 70 from pulling $CO_2$ gas from the container of acid solution source 80. Any $CO_2$ gas remaining in disinfection loop 90 is then primed to drain via PD fluid before beginning the next treatment.

The above depressurization sequence for removing $CO_2$ gas to the container of acid solution source 80 is described as being triggered via an overpressure due to the formation of $CO_2$ gas. It is also stated that the depressurization sequence may be performed one or more time. As with system 10*a*, in various embodiments for system 10*a*, (i) the triggering of the depressurization sequence and (ii) the total amount of time needed to properly dissipate the $CO_2$ gas pressure may be a function of, and depend upon, any one or more of: (a) sensed pressure in disinfection loop 90, (b) an amount of time that has passed since the start of $CO_2$ gas production or from the end of a prior depressurization sequence, (c) a volume of $CO_2$ gas to be dissipated (e.g., calculated by control unit 100 knowing citric (or other) acid concentration and disinfection fluid temperature), and/or (d) a number of prior depressurization sequences that have already taken place.

Figure 7:
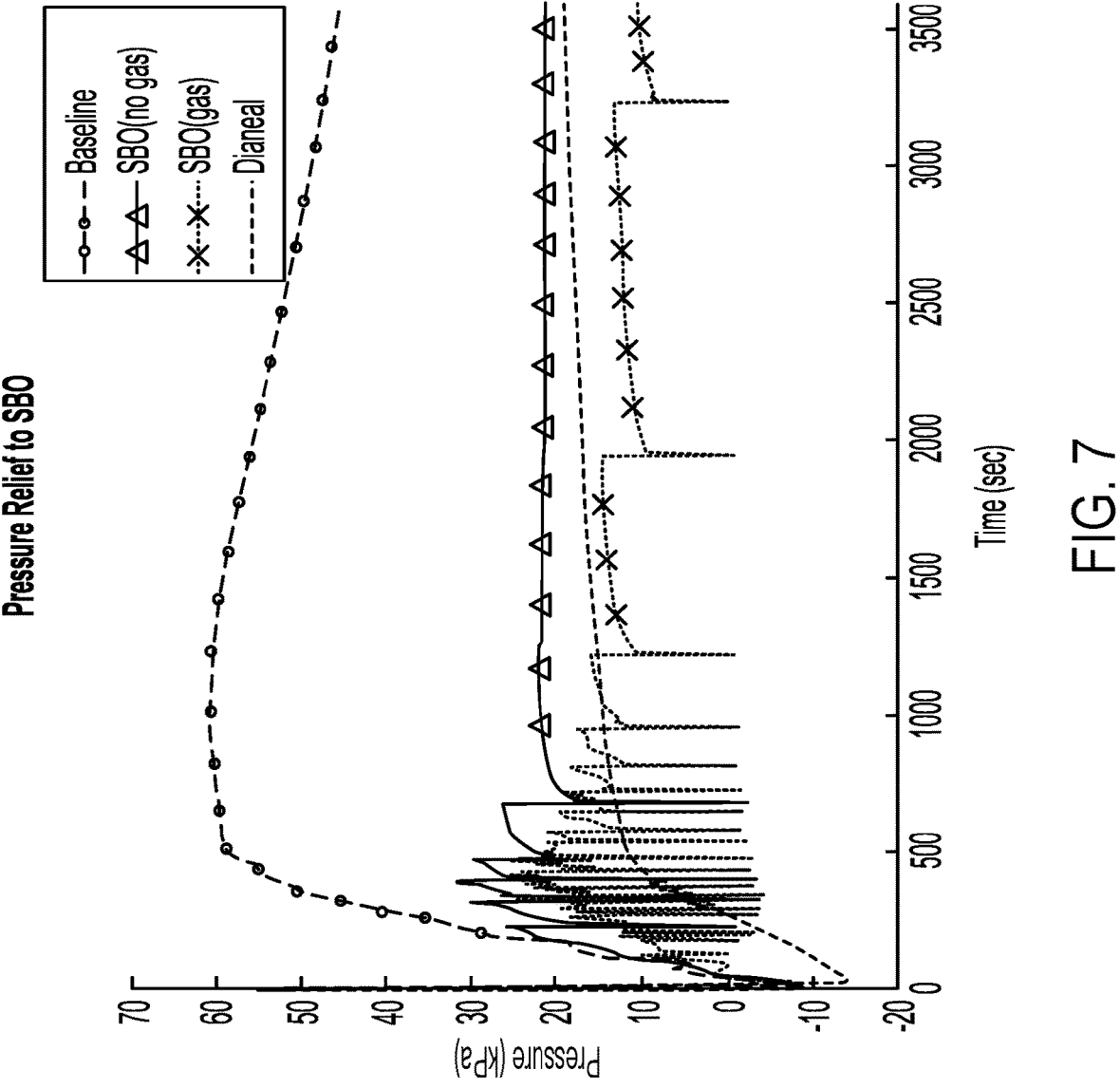
FIG. 7 is a plot versus time showing pressure relief examples using the system as associated methodology of the PD system of FIG. 6.

Referring now to FIG. 7, testing results for system 10*c* using the release $CO_2$ gas to the container of acid solution source 80 method of the present disclosure is illustrated. The top line (dotted) is a baseline showing pressures that are present from offgassed $CO_2$ when the depressurization sequence of system 10*c* is not performed. The unmarked line is for a particular PD fluid marketed by the assignee of the present disclosure, namely, Dianeal® PD fluid, which contains no bicarbonate and therefore does not need to be infused with a descaling fluid, such as citric acid during disinfection. The Δ-line and x-line are examples for PD fluids containing bicarbonate (e.g., Physioneal® PD fluid marketed by the assignee of the present disclosure), which have been combined with an acid solution, e.g., citric acid. Here, pressurized $CO_2$ gas is released to the container of acid solution source 80 upon the pressure reaching 10 kPa (1.5 psig) after 2.1 ml of 50% (by weight) of citric acid is added to the PD fluid (e.g., 300 ml) for heating and disinfection. As illustrated, the pressure increase due to offgassed $CO_2$ is mitigated and repeatedly reduced along both the Δ-line and the x-line curves. For both the Δ-line and x-line curves, the output of upper level sensor 62*a* operating with airtrap 60 is used as a limit for the release of $CO_2$ gas into acid solution source 80. The Δ-line illustrates that only a portion of the $CO_2$ gas is released into acid solution source 80 when airtrap 60 is full up to upper level sensor 62*a* with PD fluid at the start of the disinfection sequence. The x-line illustrates a more preferred curve in which there is some gas (e.g., air) already present in airtrap 60 at the beginning of the disinfection sequence. Here, $CO_2$ gas evacuation may be performed during the whole disinfection sequence, resulting in a lower pressure curve than that of the Δ-line.

It should be understood that various changes and modifications to the presently preferred embodiments described herein will be apparent to those skilled in the art. It is therefore intended that such changes and modifications be covered by the appended claims.

The invention is claimed as follows:

1. A peritoneal dialysis ("PD") system comprising:
   a PD fluid pump;
   a disinfection loop including the PD fluid pump, the disinfection loop allowing PD fluid to be used for disinfecting the disinfection loop;
   an airtrap located along the disinfection loop;
   at least one gas valve located along at least one gas line leading to an upper portion of the airtrap;
   a pressure sensor positioned and arranged to sense PD fluid pressure in the disinfection loop during a disinfection sequence; and
   a control unit, the pressure sensor outputting to the control unit, the control unit configured to cause the at least one gas valve to open when the PD fluid pressure in the disinfection loop reaches or exceeds a threshold PD fluid pressure due to gas formation caused during the disinfection sequence.

2. The PD system of claim 1, wherein the gas formation is caused by mixing the PD fluid with an acid solution.

3. The PD system of claim 1, wherein the control unit is configured such that prior to causing the at least one gas valve to open, the control unit checks that a PD fluid level in the airtrap is not too high.

4. The PD system of claim 1, which includes a drain line for draining used PD fluid during treatment, and wherein opening the at least one gas valve allows PD fluid pressure due to the gas formation to dissipate towards the drain line.

5. The PD system of claim 1, wherein the control unit is further configured to at least one of (i) close at least one PD fluid valve located adjacent to the airtrap or (ii) stop the PD fluid pump when the PD fluid pressure reaches or exceeds the threshold PD fluid pressure.

6. The PD system of claim 1, wherein the pressure sensor is located along one of the at least one gas line, which is in fluid communication with the disinfection loop, enabling the pressure sensor to sense PD fluid pressure during the disinfection sequence.

7. The PD system of claim 1, wherein the pressure sensor or a second pressure sensor outputting to the control unit senses a PD fluid pressure dissipation after opening the at least one gas valve, the control unit further configured to close the at least one gas valve and continue the disinfection sequence upon receiving an output indicative of the PD fluid pressure dissipation.

8. The PD system of claim 1, which is configured such that opening of the at least one gas valve allows gas to dissipate from the upper portion of the airtrap through one of the at least one gas line towards drain.

9. The PD system of claim 1, wherein the control unit is further configured to cause the at least one gas valve to open, or to remain open for an amount of time, based on or more of (i) gas volume, (ii) a time duration from the commencement of gas formation, and/or (iii) a number of times that the control unit has previously cause the at least one gas valve to open.

10. A peritoneal dialysis ("PD") system comprising:
a PD fluid pump;
a disinfection loop including the PD fluid pump, the disinfection loop allowing PD fluid to be used for disinfecting the disinfection loop;
an acid solution source containing an acid for use during a disinfection sequence;
a drain line positioned and arranged to drain used PD fluid during treatment;
a gas line;
at least one gas valve located along the gas line, the at least one gas valve enabling fluid communication between the gas line and the drain line;
a pressure sensor positioned and arranged to sense PD fluid pressure in the disinfection loop during the disinfection sequence; and
a control unit, the pressure sensor outputting to the control unit, the control unit configured to cause the at least one gas valve to open when the PD fluid pressure in the disinfection loop reaches or exceeds a threshold PD fluid pressure due to gas formed from mixing the PD fluid and the acid during the disinfection sequence, and wherein opening the at least one gas valve allows PD fluid pressure due to the gas formation to dissipate towards the drain line.

11. The PD system of claim 10, which includes a heater configured to heat the PD fluid and the acid during the disinfection sequence to a disinfection temperature.

12. The PD system of claim 10, wherein the PD fluid includes bicarbonate and the gas formed is carbon dioxide ("CO$_2$") gas.

13. The PD system of claim 10, which is configured such that opening of the at least one gas valve allows gas to dissipate from an upper portion of an airtrap through one of the at least one gas line towards the drain line.

14. The PD system of claim 10, wherein the control unit is configured such that prior to causing the at least one gas valve to open, the control unit checks that a PD fluid level in an airtrap is not too high.

15. The PD system of claim 10, wherein the control unit is further configured to cause the at least one gas valve to open, or to remain open for an amount of time, based on or more of (i) gas volume, (ii) a time duration from the commencement of gas formation, and/or (iii) a number of times that the control unit has previously cause the at least one gas valve to open.

16. The PD system of claim 10, wherein the control unit is further configured to maintain, at a beginning of acid dosing for the disinfection sequence, a pressure at the acid solution source that is equal to a pressure recorded at the acid solution source and at an end of acid dosing for a prior disinfection sequence.

17. A peritoneal dialysis ("PD") system comprising:
a PD fluid pump;
a disinfection loop including the PD fluid pump, the disinfection loop allowing PD fluid to be used for disinfecting the disinfection loop;
an airtrap located along the disinfection loop;
at least one gas valve located along at least one gas line leading to an upper portion of the airtrap;
a pressure sensor positioned and arranged to sense PD fluid pressure in the disinfection loop during a disinfection sequence; and
a control unit, the pressure sensor outputting to the control unit, the control unit configured to cause the at least one gas valve to open and the PD fluid pump to pump an amount of gas from the airtrap when the PD fluid pressure in the disinfection loop reaches or exceeds a threshold PD fluid pressure due to gas formation caused during the disinfection sequence.

18. The PD system of claim 17, which includes a patient line valve located along a patient line, and wherein the control unit causes the patient line valve to be open when the PD fluid pump pumps the amount of gas from the airtrap.

19. The PD system of claim 18, which includes a drain line valve located along a drain line, and wherein the control unit causes the patient line valve to be closed and the drain line valve to be open after the PD fluid pump pumps the amount of gas from the airtrap so as to deliver the gas to the drain line.

20. The PD system of claim 17, wherein the control unit is further configured to cause the at least one gas valve to open and the PD fluid pump to pump, or to remain open for an amount of time while the PD fluid pumps, based on or more of (i) gas volume, (ii) a time duration from the commencement of gas formation, and/or (iii) a number of times that the control unit has previously cause the at least one gas valve to open.

* * * * *